(12) United States Patent
Johnson et al.

(10) Patent No.: US 8,933,179 B2
(45) Date of Patent: Jan. 13, 2015

(54) METHOD OF PRODUCING ARCYLIC AND METHACRYLIC ACID

(75) Inventors: David William Johnson, Redcar (GB); Graham Ronald Eastham, Redcar (GB); Martyn Poliakoff, Beeston (GB); Thomas Andrew Huddle, Guildford (GB)

(73) Assignee: Lucite International UK Limited, Hampshire (GB)

( * ) Notice: Subject to any disclaimer, the term of this patent is extended or adjusted under 35 U.S.C. 154(b) by 87 days.

(21) Appl. No.: 13/517,958

(22) PCT Filed: Dec. 21, 2010

(86) PCT No.: PCT/GB2010/052176
§ 371 (c)(1),
(2), (4) Date: Aug. 16, 2012

(87) PCT Pub. No.: WO2011/077140
PCT Pub. Date: Jun. 30, 2011

(65) Prior Publication Data
US 2012/0309911 A1 Dec. 6, 2012

(30) Foreign Application Priority Data

Dec. 21, 2009 (GB) .................................. 0922255.5

(51) Int. Cl.
*C07C 51/38* (2006.01)
*C08F 220/10* (2006.01)
(Continued)

(52) U.S. Cl.
CPC ................. *C07C 51/38* (2013.01); *C07C 67/08* (2013.01); *C08F 220/14* (2013.01)
USPC .............. 526/75; 562/598; 562/599; 560/205

(58) Field of Classification Search
USPC ................................................. 562/598, 599
See application file for complete search history.

(56) References Cited

U.S. PATENT DOCUMENTS 2,902,512 A * 9/1959 Verheyden et al. ............ 562/598
3,960,901 A * 6/1976 Berg .............................. 549/261
(Continued)

FOREIGN PATENT DOCUMENTS

DE   102 03 565    7/2003
EP   0 716 122     6/1996
(Continued)

OTHER PUBLICATIONS

J. S. Chamberlain "A Textbook of Organic Chemistry," published by Philadelphia P. Blakiston's Son & Co. in 1921, p. 299.*
(Continued)

*Primary Examiner* — Vu A Nguyen
(74) *Attorney, Agent, or Firm* — Venable LLP; Keith G. Haddaway; Lars H. Genieser

(57) ABSTRACT

A method of producing a compound of formula (i): wherein R=H or CH₃ the method comprising exposing a source of a compound of formula (ii) to reaction conditions of temperature and pressure: formula (ii) wherein R is defined as above wherein, when R=CH₃, the source of a compound of formula (ii) is exposed to reaction conditions of temperature and pressure while being in a liquid phase.

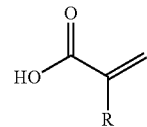

(i)

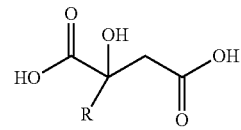

(ii)

16 Claims, 1 Drawing Sheet

(51) Int. Cl.
*C08F 120/10* (2006.01)
*C07C 57/04* (2006.01)
*C07C 67/00* (2006.01)
*C07C 67/08* (2006.01)
*C08F 220/14* (2006.01)

(56) References Cited

U.S. PATENT DOCUMENTS 5,612,417 A 3/1997 Rhein et al.
2005/0085607 A1 4/2005 Kabs et al.
2010/0317887 A1 12/2010 Meisenburg et al.

FOREIGN PATENT DOCUMENTS

WO WO-99/52628 A1 10/1999
WO WO-2009/106550 9/2009
WO WO-2010/058119 A1 5/2010

OTHER PUBLICATIONS

Carlsson et al. Ind. Eng. Chem. Res. 1994, 33, 1989-1996.*
A. Michael and G. Tissot (Journal für Praktische Chemie, 46(1), Nov. 8, 2004, 285-304).*
Carlsson et al., "Study of the Sequential Conversion of Citric to Itaconic to Mthacrylic Acid in Near-Critical and Supercritical Water," Ind. Eng. Chem. Res., vol. 33, pp. 1989-1996 (1994).

Office Action issued in Singapore Application No. 201204381-6 dated Sep. 16, 2013.
Letter dated Oct. 23, 2013 reporting Office Action issued in Mexican Application No. MX/a/2012/006963.
Office Action issued in Australian Application No. 2010334633 dated Oct. 25, 2013.
Office Action issued in Eurasian Application No. 201290550/28 dated Oct. 30, 2013.
Examination Report issued in Pakistani Application No. 1060/2010 received Nov. 22, 2012.
First Examination Report issued in New Zealand Application No. 601040 dated Mar. 19, 2013.
Office Action issued in European Application No. 10803132.9 dated Oct. 25, 2012.
International Preliminary Report on Patentability issued in Application No. PCT/GB2010/052176 dated Jul. 5, 2012.
Office Action issued in Chinese Patent Application No. 201080057627.0 dated Jan. 10, 2014.
Office Action issued in Mexican Patent Application No. MX/a/2012/006963 dated Apr. 7, 2014.
Office Action issued in New Zealand Patent Application No. 601040 dated Mar. 19, 2013.
Office Action issued in Ukrainian Patent Application No. a 2012 07652 dated May 15, 2014.

* cited by examiner

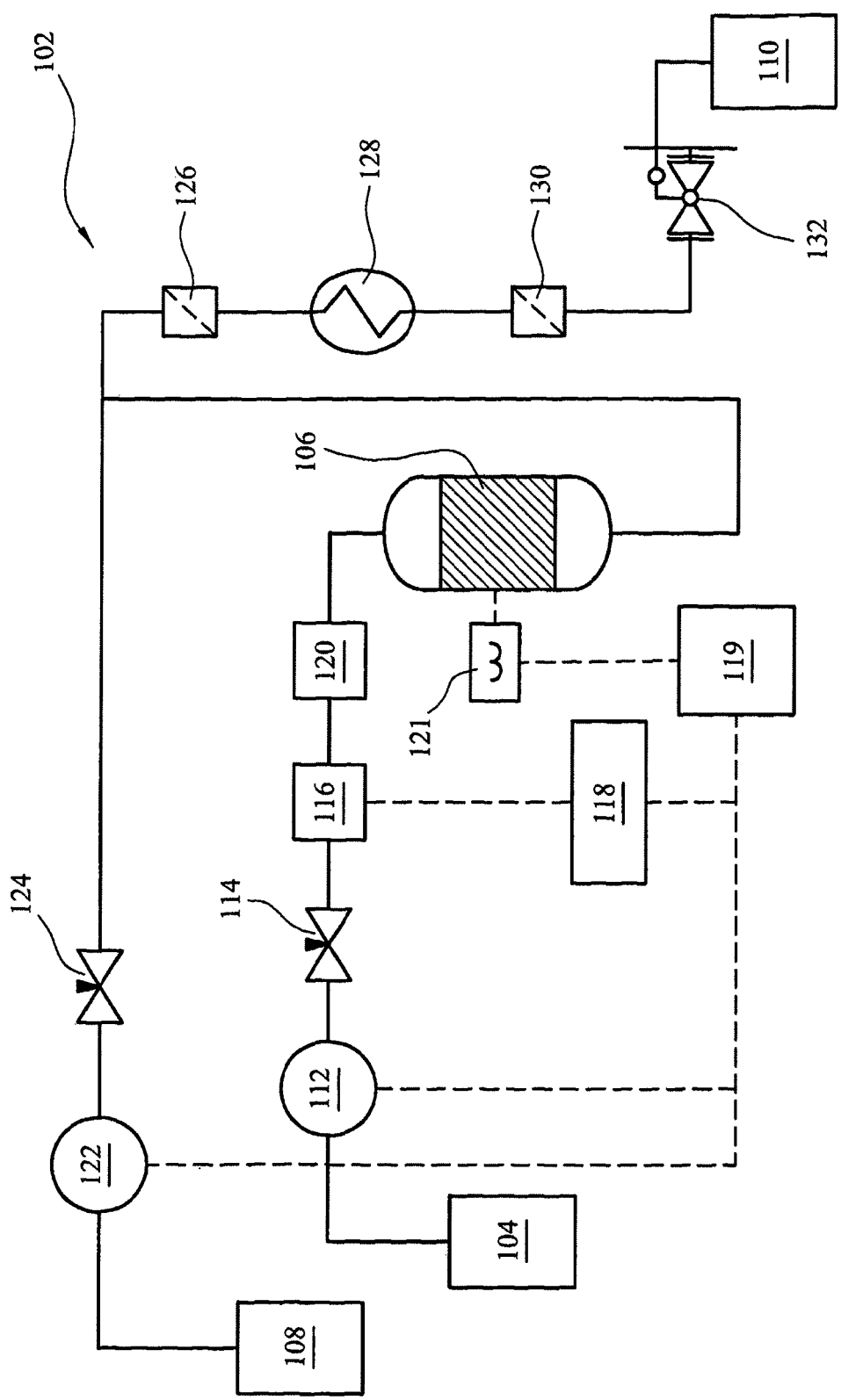

METHOD OF PRODUCING ARCYLIC AND METHACRYLIC ACID

The present invention relates to a method of producing acrylic and methacrylic acid, and extends to acrylic and methacrylic acid produced by the method and to their alkyl esters, especially methyl methacrylate.

Acrylic acid (prop-2-enoic acid, AA) and methacrylic acid (2-methyl prop-2-enoic acid, MAA) are important industrial chemicals, principally as a precursor to their esters, such as methyl acrylate (MA) and methyl methacrylate (MMA), for example. Their main application is in the production of plastics for various applications. The most significant polymerisation application is the casting, moulding or extrusion of polymethyl methacrylate (PMMA) to produce high optical clarity plastics. In addition, many copolymers are used, important copolymers are copolymers of methyl methacrylate with α-methyl styrene, ethyl acrylate and butyl acrylate. Currently MMA, MAA and AA are produced entirely from petrochemical feedstocks.

MAA and MMA are produced on a large industrial scale by various methods. For example, the acetone cyanohydrin (ACH) route, which uses acetone and hydrogen cyanide as reactants and wherein the intermediate cyanohydrin is converted with sulphuric acid to a sulphate ester of the methacrylamide, methanolysis of which gives ammonium bisulphate and MMA. However, this method is not only expensive, but both reactants, especially hydrogen cyanide represents a significant health and safety risk and the process produces large amounts of unwanted ammonium sulphate as a byproduct. Alternatively, in a further process, it is known to start with an isobutylene or, equivalently, tert-butanol reactant which is then oxidized to methacrolein and then to methacrylic acid.

More recently, it has been known to produce MMA directly by a two stage process by the carbonylation of ethylene to form methyl propionate, followed by reaction with formaldehyde to yield MMA. This process is known as the Alpha process. Stage I is described in WO96/19434 and relates to the use of 1,2-bis-(di-t-butylphosphinomethyl)benzene ligand in the palladium catalysed carbonylation of ethylene to methyl propionate in high yield and selectivity. The applicant has also developed a process for the catalytic conversion of methyl propionate (MEP) to MMA using formaldehyde. A suitable catalyst for this is a caesium catalyst on a support, for instance, silica. However, whilst this route to MMA provides good product selectivity and is relatively cheap, the reactants, particularly ethylene, are sourced as a fraction of naturally occurring crude oil.

For many years, biomass has been offered as an alternative to fossil fuels both as a potential alternative energy resource and as an alternative resource for chemical process feedstocks. Accordingly, one obvious solution to the reliance on fossil fuels is to carry out any of the known processes for the production of MMA or methacrylic acid using a biomass derived feedstock.

In this regard, it is well known that syngas (carbon monoxide and hydrogen) can be derived from Biomass and that methanol can be made from syngas. Several Industrial plants produce methanol from syngas on this basis, for example, at Lausitzer Analytik GmbH Laboratorium für Umwelt and Brennstoffe Schwarze Pumpe in Germany, Biomethanol Chemie Holdings, Delfzijl, Netherlands. Nouri and Tillman, Evaluating synthesis gas based biomass to plastics (BTP) technologies, (ESA-Report 2005:8 ISSN 1404-8167) teach the viability of using methanol produced from synthesis gas as a direct feedstock or for the production of other feedstocks such as formaldehyde. There are also many patent and non-patent publications on production of syngas suitable for production of chemicals from biomass.

The production of ethylene by dehydration of biomass derived ethanol is also well established with manufacturing plants in, especially, Brazil.

The production of propionic acid from carbonylation of ethanol and the conversion of biomass derived glycerol to molecules such as acrolein and acrylic acid is also well established in the patent literature.

Thus ethylene, carbon monoxide and methanol have well established manufacturing routes from biomass. The chemicals produced by this process are either sold to the same specification as oil/gas derived materials, or are used in processes where the same purity is required.

Thus in principle there is no barrier to operation of the so called Alpha process above to produce methyl propionate from Biomass derived feedstocks. In fact, its use of simple feedstocks such as ethylene, carbon monoxide and methanol rather sets it apart as an ideal candidate.

Acrylic acid may be produced from propene or by the hydrocarboxylation of acetylene Both of these methods require starting materials that are most readily available as fractions of crude oil.

In this regard, WO2010/058119 relates explicitly to the use of biomass feedstocks for the above Alpha process and the catalytic conversion of methyl propionate (MEP) produced to MMA using formaldehyde. These MEP and formaldehyde feedstocks could come from a biomass source as mentioned above. However, such a solution still involves considerable processing and purification of the biomass resource to obtain the feedstock which processing steps themselves involve the considerable use of fossil fuels.

Further, the Alpha process requires multiple feedstocks in one location which can lead to availability issues. It would therefore be advantageous if any biochemical route avoided multiple feedstocks or lowered the number of feedstocks.

Therefore, an improved alternative non-fossil fuel based route to acrylate monomers such as methyl methacrylate, acrylic acid and methacrylic acid is still required.

With the abundance and availability of crude oil declining and the detrimental environmental impact of recovering crude oil, the cost of the raw materials to pursue this route are set to increase.

There is, therefore, a desire to find a route to producing alkyl acrylate and methacrylate, or their immediate precursors, such as acrylic and methacrylic acid, that is cheap and efficient and does not use any fraction of crude oil as a reactant.

It is an object of aspects of the present invention to address the above mentioned or other problems and to provide one or more solutions.

According to a first aspect of the present invention there is provided a method of producing a compound of formula (i):

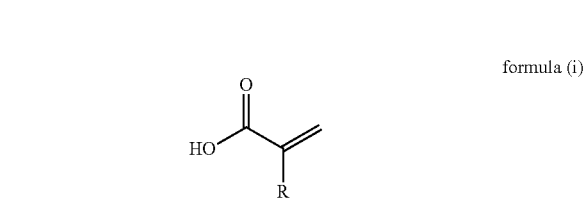

formula (i)

wherein R=H or CH$_3$
the method comprising exposing a source of a compound of formula (ii) to reaction conditions of temperature and pressure:

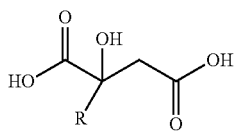

formula (ii)

wherein R is defined as above
wherein, when R=CH$_3$, the source of a compound of formula (ii) is exposed to reaction conditions of temperature and pressure while being in a liquid phase.

Advantageously, it has been found that under certain conditions of temperature and pressure, compounds of formula (ii) decompose into various components, one of which being the compound of formula (i). It will be appreciated that a compound of formula (i) wherein R=H represents acrylic acid, and a compound of formula (i) wherein R=CH$_3$ represents methacrylic acid. Accordingly, the present invention represents an alternative route to acrylic and methacrylic acids.

The compounds of formula (ii) are available from non-fossil fuel sources. For instance, the compound wherein R=CH$_3$ could be produced from citric acid by decarboxylation at suitably high temperatures. Citric acid may be produced from known fermentation processes. Accordingly, the process of the invention goes some way to providing a biological or part biological route to generate acrylates directly whilst minimising reliance on fossil fuels.

Preferably, the reaction conditions comprise a temperature of at least 100° C., more preferably at least 150° C., more preferably at least 175° C., more preferably at least 200° C. and yet more preferably at least 225° C.

Preferably, the reaction conditions comprise a temperature of less than about 550° C., more preferably less than about 500° C., more preferably less than about 475° C., more preferably less than about 450° C., and yet more preferably less than about 425° C.

Preferably, the reaction conditions comprise a temperature of between about 200 and 450° C., more preferably between about 225° C. and 425° C. and most preferably between about 250° C. and 400° C.

Preferably, the reaction conditions comprise a temperature at which the reaction medium is in the liquid phase.

To maintain the reactants in the liquid phase under the above temperature conditions the reaction is carried out at suitable pressures in excess of atmospheric pressure. Suitable pressures which will maintain the reactants in the liquid phase in the above temperature ranges are greater than 200 psi, more suitably, greater than 300 psi, most suitably, greater than 450 psi and in any case at a higher pressure than that below which the reactant medium will boil. There is no upper limit of pressure but the skilled person will operate within practical limits and within apparatus tolerances, for instance, at less than 10,000 psi, more typically, at less than 5,000 psi, most typically, at less than 4000 psi.

Preferably, the reaction is at a pressure of between about 200 and 10000 psi. More preferably, the reaction is at a pressure of between about 300 and 5000 psi and yet more preferably between about 450 and 3000 psi.

In a preferred embodiment, the reaction is at a pressure at which the reaction medium is in the liquid phase.

Preferably, the reaction conditions comprise a temperature and pressure at which the reaction medium is in the liquid phase.

Preferably, the source of a compound of formula (ii) is exposed to reaction conditions of temperature and pressure in the presence of a catalyst.

The catalyst may be a base catalyst, an acid catalyst or an acid and base catalyst.

Preferably, where the catalyst comprises a base catalyst, the catalyst comprises a source of OH$^-$ ions. Preferably, the base catalyst comprises a metal oxide, hydroxide, carbonate, acetate (ethanoate), alkoxide or hydrogencarbonate, or a metal salt of a decomposable di- or tri-carboxylic acid, or a quaternary ammonium compound of one of the above; more preferably a Group I or Group II metal oxide, hydroxide, carbonate, acetate, alkoxide, hydrogencarbonate, or metal salt of a di- or tri-carboxylic acid. The base may comprise one or more amine. Preferably, the base is selected from one or more of the following: LION, NaOH, KOH Mg(OH)$_2$, Ca(OH)$_2$, Ba(OH)$_2$, CsOH, Sr(OH)$_2$, RbOH, NH$_4$OH, Li$_2$CO$_3$, Na$_2$CO$_3$, K$_2$CO$_3$, Rb$_2$CO$_3$, Cs$_2$CO$_3$, MgCO$_3$, CaCO$_3$, SrCO$_3$, BaCO$_3$, (NH$_4$)$_2$CO$_3$, LiHCO$_3$, NaHCO$_3$, KHCO$_3$, RbHCO$_3$, CsHCO$_3$, Mg(HCO$_3$)$_2$, Ca(HCO$_3$)$_2$, Sr(HCO$_3$)$_2$, Ba(HCO$_3$)$_2$, NH$_4$HCO$_3$, Li$_2$O, Na$_2$O, K$_2$O, Rb$_2$O, Cs$_2$O, MgO, CaO, SrO, BaO, Li(OR$^1$), Na(OR$^1$), K(OR$^1$), Rb(OR$^1$), Cs(OR$^1$), Mg(OR$^1$)$_2$, Ca(OR$^1$)$_2$, Sr(OR$^1$)$_2$, Ba(OR$^1$)$_2$, NH$_4$(OR$^1$) where R$^1$ is any C$_1$ to C$_6$ branched, unbranched or cyclic alkyl group, being optionally substituted with one or more functional groups; Li(RCO$_2$), Na(RCO$_2$), K(RCO$_2$), Rb(RCO$_2$), Cs(RCO$_2$), Mg(RCO$_2$)$_2$, Ca(RCO$_2$)$_2$, Sr(RCO$_2$)$_2$ or Ba(RCO$_2$)$_2$, where RCO$_2$ is selected from itaconate, citrate, oxalate or acetate; methylamine, ethylamine, propylamine, butylamine, pentylamine, hexylamine, cyclohexylamine, aniline, or R$_4$NOH where R is selected from methyl, ethyl propyl or butyl. More preferably, the base is selected from one or more of the following: LiOH, NaOH, KOH, Mg(OH)$_2$, Ca(OH)$_2$, Ba(OH)$_2$, CsOH, Sr(OH)$_2$, RbOH, NH$_4$OH, Li$_2$CO$_3$, Na$_2$CO$_3$, K$_2$CO$_3$, Rb$_2$CO$_3$, Cs$_2$CO$_3$, MgCO$_3$, CaCO$_3$, (NH$_4$)$_2$CO$_3$, LiHCO$_3$, NaHCO$_3$, KHCO$_3$, RbHCO$_3$, CsHCO$_3$, Mg(HCO$_3$)$_2$, Ca(HCO$_3$)$_2$, Sr(HCO$_3$)$_2$, Ba(HCO$_3$)$_2$, NH$_4$HCO$_3$, Li$_2$O, Na$_2$O, K$_2$O, Rb$_2$O, Cs$_2$O; Li(RCO$_2$), Na(RCO$_2$), K(RCO$_2$), Rb(RCO$_2$), Cs(RCO$_2$), Mg(RCO$_2$)$_2$, Ca(RCO$_2$)$_2$, Sr(RCO$_2$)$_2$ or Ba(RCO$_2$)$_2$, where RCO$_2$ is selected from itaconate, citrate, oxalate or acetate; tetramethylammonium hydroxide, or tetraethylammonium hydroxide. Most preferably, the base is selected from one or more of the following: NaOH, KOH, Ca(OH)$_2$, CsOH, RbOH, NH$_4$OH, Na$_2$CO$_3$, K$_2$CO$_3$, Rb$_2$CO$_3$, Cs$_2$CO$_3$, MgCO$_3$, CaCO$_3$, (NH$_4$)$_2$CO$_3$, Na(RCO$_2$), K(RCO$_2$), Rb(RCO$_2$), Cs(RCO$_2$), Mg(RCO$_2$)$_2$, Ca(RCO$_2$)$_2$, Sr(RCO$_2$)$_2$ or Ba(RCO$_2$)$_2$, where RCO$_2$ is selected from itaconate, citrate or oxalate; or tetramethylammonium hydroxide.

Examples of acid catalysts include proton acid catalysts and Lewis acid catalysts. In a preferred embodiment, the proton acid catalysts suitable for use in the present process include but are not limited to hydrochloric acid, nitric acid, acetic acid, sulfuric acid, trifluoromethanesulfonic acid, trifluoracetic acid. Said acid catalyst may comprise a heterogeneous source of acids such as strongly acidic ion exchange resins of the sulfonic type. Examples of commercially available strongly acidic ion exchange resins of the sulfonic type are those known by the trade names AMBERLYST A15, AMBERLYST 38 W, AMBERLYST 36, AMBERJET 1500H, AMBERJET 1200H, (AMBERJET is a trademark of Rohm and Haas Company) DOWEX MSC-1, DOWEX 50W (DOWEX is a trademark of Dow Chemical Company), DELOXAN ASP I/9 (DELOXAN is a trademark of Evonik), DIAION SK1B (DIAION is a trademark of Mitsubushi), LEWATIT VP OC 1812, LEWATIT S 100 MB, LEWATIT S 100 G1 (LEWATIT is a trademark of Bayer), NAFION SAC13, NAFION NR50 (NAFION is a trademark of DuPont) and CT275 (a macroporous resin with a medium pore diameter in the range of from 600 to 750, available from Purlite). In another embodiment, suitable Lewis acid catalysts include but are not limited to $ZnCl_2$, $BeCl_2$, $TiCl_4$, $SnCl_4$, $FeCl_3$, $FeCl_2$, $SbCl_5$, $AlCl_3$ and other metal halides. Co-catalysts such as acetic acid may also be used in the process according to the invention.

Examples of acid and base catalysts include porous high surface area silica containing 1-10% by weight of an alkali metal (expressed as metal), wherein the catalyst contains at least one modifier element selected from boron, magnesium, aluminium, zirconium and hafnium. Examples of such catalysts are explained in detail in WO 99/52628, the details of which being incorporated herein by reference.

The catalyst may be homogeneous or heterogeneous. In one embodiment, the catalyst may be dissolved in a liquid reaction phase. However, the catalyst may be suspended on a solid support over which the reaction phase may pass. In this scenario, the reaction phase is preferably maintained in a liquid, more preferably, an aqueous phase.

The process of the present invention may be a batch or continuous process.

Advantageously, one by-product may be 2-hydroxy isobutyric acid (HIB) which exists in equilibrium with the product MAA. Accordingly, extraction of the MAA shifts the equilibrium from HIB to MAA thus generating further MAA during the process.

In the present invention, where $R=CH_3$, the compound of formula (ii) is citramalic acid and where $R=H$, the compound of formula (ii) is malic acid.

Preferably, the source of a compound of formula (ii) comprises the dicarboxylic acid of formula (ii), but may also, additionally or alternatively, comprise one or more of salt, being any Group I or Group II metal salt.

Preferably, the source of a compound of formula (ii) is exposed to the reaction conditions for a time period of at least 0.01 seconds, more preferably at least about 0.05 seconds, yet more preferably at least about 0.1 seconds and most preferably at least about 1 second.

Preferably, the source of a compound of formula (ii) is exposed to the reaction conditions for a time period of less than about 1000 seconds, more preferably less than about 500 seconds, yet more preferably less than about 300 seconds.

Preferably, the source of a compound of formula (ii) is exposed to the reaction conditions for a time period of between about 0.1 seconds and 300 seconds, more preferably between about 0.5 seconds and 250 seconds and most preferably between about 1 second and 200 seconds.

Preferably, the source of a compound of formula (ii) further comprises water. Preferably, the source of a compound of formula (ii) is aqueous. Preferably, the reaction occurs under aqueous conditions.

Preferably, the concentration of the source of a compound of formula (ii) is at least 0.001M, preferably in an aqueous source thereof; more preferably at least about 0.005M, preferably in an aqueous source thereof; more preferably at least about 0.01M, preferably in an aqueous source thereof.

Preferably, the concentration of the source of a compound of formula (ii) is less than about 10M, preferably in an aqueous source thereof; more preferably, less than about 5M, preferably in an aqueous source thereof; more preferably less than about 1M, preferably in an aqueous source thereof.

Preferably, the concentration of the source of a compound of formula (ii) is in the range 0.001M-10M, more preferably, 0.005M-5M, most preferably, 0.01M-1M, preferably in an aqueous source thereof.

The catalyst may be dissolvable in a liquid medium, which may be water. The catalyst may be dissolvable in the reaction mixture. The catalyst may be in an aqueous solution. Preferably, the concentration of the catalyst in the reaction mixture is at least about 0.0001M, more preferably at least about 0.0005M, more preferably at least about 0.001M.

Preferably, the concentration of the catalyst in the reaction mixture is less than about 5M, more preferably, less than about 1M, more preferably less than about 0.5M.

Preferably, the concentration of the catalyst in the reaction mixture is in the range 0.0001M-5M, more preferably, 0.0005M-1M, most preferably, 0.001M-0.5M, preferably in an aqueous source thereof. In any case, if the reaction is in aqueous solution, the catalyst concentration is preferably less than or equal to that which would amount to a saturated solution at the temperature and pressure of the reaction.

Preferably, the relative concentration of the source of a compound of formula (ii) to the concentration of catalyst is between about 100:1 and 1:100, more preferably between about 10:1 and 1:10, and yet more preferably between about 5:1 and 1:5.

In a most preferred embodiment, the relative concentration of the source of a compound of formula (ii) to the concentration of catalyst is between about 3:1 and 1:1, for example, preferably about 2:1.

Preferably, the reaction conditions are generally acidic. Preferably, the reaction conditions comprise a pH of between about 1 and about 6, more preferably between about 2 and about 5.

According to a further aspect of the present invention, there is provided a method of converting malic acid to acrylic acid, the method comprising exposing a source of malic acid to reaction conditions of pressure and temperature.

According to a further aspect of the present invention, there is provided a method of converting citramalic acid to methacrylic acid, the method comprising exposing a source of citramalic acid in the liquid phase to reaction conditions of pressure and temperature.

According to a further aspect of the present invention there is provided a compound of formula (i) produced by any of the above aspects.

According to a further aspect of the present invention there is provided a method of producing an alkyl ester of a compound of figure (i), the method comprising esterification of the compound of formula (i) formed by any of the above aspects.

According to a further aspect of the present invention there is provided a method of producing polymethylmethacrylate (PMMA), the method comprising esterification of methacrylic acid formed by any of the above aspects to form methyl methacrylate, followed by polymerisation of the said methyl methacrylate.

According to a further aspect of the present invention there is provided polymethylmethacrylate (PMMA) formed from the method of the above aspect.

As mentioned above, the methacrylic acid or acrylic acid product may be esterified to produce an ester thereof. Potential esters may be selected from $C_1$-$C_{12}$ alkyl or $C_2$-$C_{12}$ hydroxyalkyl, glycidyl, isobornyl, dimethylaminoethyl, tripropyleneglycol esters.

According to a further aspect of the present invention there is provided a method of preparing polymers or copolymers of methacrylic acid, acrylic acid, methacrylic acid esters and acrylic acid esters comprising the steps of
(i) preparation of a compound of formula (i) in accordance with the first aspect of the present invention;
(ii) optional esterification of the compound prepared in step (i) to produce the corresponding ester;
(iii) polymerisation of the compound prepared in step (i) and/or the ester prepared in step (ii), optionally with one or more comonomers, to produce polymers or copolymers thereof.

Preferably, the ester of (ii) above is selected from C1-C12 alkyl or C2-C12 hydroxyalkyl, glycidyl, isobornyl, dimethylaminoethyl, tripropyleneglycol acrylic and methacrylic esters, more preferably, ethyl, n-butyl, i-butyl, hydroxymethyl, hydroxypropyl or methyl acrylate and methacrylate, most preferably, methyl methacrylate.

Advantageously, such polymers will have an appreciable portion if not all of the monomer residues derived from a source other than fossil fuels.

In any case, preferred comonomers include for example, monoethylenically unsaturated carboxylic acids and dicarboxylic acids and their derivatives, such as esters, amides and anhydrides.

Particularly preferred comonomers are acrylic acid, methyl acrylate, ethyl acrylate, propyl acrylate, n-butyl acrylate, iso-butyl acrylate, t-butyl acrylate, 2-ethylhexyl acrylate, hydroxyethyl acrylate, iso-bornyl acrylate, methacrylic acid, methyl methacrylate, ethyl methacrylate, propyl methacrylate, n-butyl methacrylate, iso-butyl methacrylate, t-butyl methacrylate, 2-ethylhexyl methacrylate, hydroxyethyl methacrylate, lauryl methacrylate, glycidyl methacrylate, hydroxypropyl methacrylate, iso-bornyl methacrylate, dimethylaminoethyl methacrylate, tripropyleneglycol diacrylate, styrene, α-methyl styrene, vinyl acetate, acrylonitrile, butadiene, butadiene and styrene (MBS) and ABS subject to any of the above comonomers not being the momomer selected from methacrylic acid or a methacrylic acid ester in (i) or (ii) above in any given copolymerisation of the said acid monomer in (i) or a said ester monomer in (ii) with one or more of the comonomers.

It is of course also possible to use mixtures of different comonomers. The comonomers themselves may or may not be prepared by the same process as the monomers from (i) or (ii) above.

The invention also extends to block copolymers prepared from the further aspect monomers of (i) or (ii) above together with optional comonomers and one or more initial polymer or copolymer blocks and/or added polymerised or copolymerised blocks.

According to a further aspect of the present invention there is provided polymethylmethacrylate (PMMA) homopolymers or copolymers formed from the method of the above aspect.

For the avoidance of doubt, by the term citramalic acid, is meant the following compound of formula (iii)

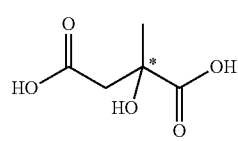

formula (iii)

Citramalic acid has a chiral centre at "*", however, for the purposes of the present invention it is unimportant whether "R" or "S" citramalic acid is used.

For the avoidance of doubt, by the term malic acid, is meant the following compound of formula (iv)

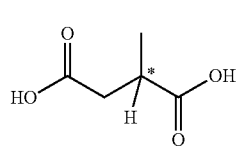

formula (iv)

Malic acid has a chiral centre at "*", however, for the purposes of the present invention it is unimportant whether "R" or "S" malic acid is used.

All of the features contained herein may be combined with any of the above aspects, in any combination.

For a better understanding of the invention, and to show how embodiments of the same may be carried into effect, reference will now be made, by way of example, to the following figures and examples.

FIG. 1 shows a diagrammatic representation of a possible reactor.

Referring to FIG. 1 there is shown a diagrammatic representation of a reaction scheme 102. In broad terms, a reaction mixture from vessel 104 flows through a reactor 106, is quenched by a flow of quench water from vessel 108 and is deposited into a collection vessel 110.

In more detail, a reaction mixture of aqueous citramalic acid comprising an amount of catalyst is pumped from vessel 104 by a pump 112 via a valve 114, a pressure monitor 116 (being connected to a pressure trip 118) and a pressure relief valve 120 to a reactor vessel 106. The reactor vessel 106 is connected to a temperature controller 119 and heater 121 to alter the temperature conditions therewithin. The products leave the reactant and are quenched by a flow of cold water from vessel 108 (which is driven by a quench pump 122, via a valve 124). The quenched products proceed via a first filter 126, a heat exchanger 128 and a second filter 130 to a back pressure regulator 132 and into a collection vessel 110.

The speed of the pumps 112 and 122 may be altered and the temperature of the reactor closely controlled to alter reaction conditions within the reaction vessel 106 and residence time within the reactor vessel 106.

EXAMPLES

The following examples were undertaken as follows. A precursor solution is prepared by dissolving solid (R)-(–)-citramalic acid (commercially available from VWR International) with a sodium hydroxide catalyst in nano-pure water to the required concentration.

The precursor solution is pumped into the system using a Gilson analytical HPLC pump. The solution is pumped into a heater unit (coil of pipe with heated core and jacket), which is itself housed in an oven. The oven serves to reduce temperature variations of the heater unit by providing an increased ambient environmental temperature. The oven temperature in the following examples is fixed at a temperature of 200° C., but the heater unit is set to the desired reaction temperature.

After leaving the heater, the resultant product flow is directed out of the oven and mixed with a second flow of water (at room temperature) in order to quench further reaction. The quenching water is introduced into the system via a second Gilson HPLC pump. The reactor volume is considered to be that between the start of the heater and the quenching point.

The quenched product solution is then passed through a heat exchanger to reduce the temperature further, before leaving the system through a back pressure regulator for collection and analysis.

Analysis of the products in the liquid phase is conducted using high-pressure liquid chromatography. All products known to occur are pre-calibrated on the HPLC system, and linear concentration response ranges for each compound are established. For the analysis of a sample, further dilution is usually required to yield concentrations that lie within these linear response ranges. Resolution of compounds in the HPLC analysis is achieved using a Phenomex RHM-monosaccharide column and a 0.0005M $H_2SO_4$ mobile phase.

Gaseous products (not limited to carbon dioxide) are also known to be formed in this reaction. Qualitative detection of these products is conducted via gas chromatography using a Varian CP-4900 microGC. However, these products are currently not accounted for quantitatively and therefore are not reported in these results. It is acknowledged that this will influence the values of the reported mass balances.

Product yields are expressed as absolute mole percent (100×moles product/mole of reactant fed)

Experiment 1

Citramalic acid decomposition at 250° C.
Conditions:

| Precursor: | 0.01M Citramalic acid |
|---|---|
| Catalyst: | 0.005M sodium Hydroxide |
| Temperature: | 250° C. |
| Pressure: | 5070 psi |

The results for experiment 1 at different residence times is shown in table 1, below.

TABLE 1

| Residence Time (s) | CM conversion (%) | MA yield (%) |
|---|---|---|
| 23.5 | 25.96 | 17.87 |
| 64.3 | 70.85 | 32.26 |
| 123.1 | 100.00 | 33.52 |
| 190.6 | 100.00 | 18.03 |

Key:
CM = Citramalic acid
MA = Methacrylic acid

Experiment 2

Citramalic acid decomposition at 300° C.
Conditions:

| Precursor: | 0.01M Citramalic acid |
|---|---|
| Catalyst: | 0.005M sodium Hydroxide |
| Temperature: | 300° C. |
| Pressure: | 5070 psi |

The results for experiment 2 at different residence times is shown in table 2, below.

TABLE 2

| Residence Time (s) | CM conversion (%) | MA yield (%) |
|---|---|---|
| 21 | 100.00 | 80.80 |
| 63.9 | 100.00 | 24.50 |
| 1234.6 | 100.00 | 36.94 |
| 191.7 | 100.00 | 31.69 |

As is shown in the experimental results above, citramalic acid is converted into methacrylic acid in a one step process by exposing it to excess heat and pressure in the presence of a basic catalyst.

Experiment 3

In experiment 3, the decomposition of malic acid was undertaken using the method of examples 1 and 2, but the pH was varied to asses the effect of pH on the levels of acrylic acid production.
Conditions:

| Precursor | 0.1M Malic Acid |
|---|---|
| Catalyst | [NaOH] - Variable |
| Temperature | 260° C. |
| Residence time | 350 seconds |
| Pressure | 5070 psi |

The results of experiment 3 at different pH levels (by varying the concentration of NaOH catalyst), are show below in table 3.

TABLE 3

| pH | Malic Acid Conversion | Acrylic Acid Yield | Maleic Acid Yield | Fumaric Acid Yield |
|---|---|---|---|---|
| 2.12 | 42.11 | 0.88 | 8.20 | 12.60 |
| 2.52 | 43.36 | 2.16 | 11.35 | 15.77 |
| 2.72 | 50.73 | 3.26 | 13.73 | 18.92 |
| 3.19 | 55.19 | 6.37 | 20.42 | 29.44 |
| 3.9 | 68.04 | 7.87 | 20.53 | 33.34 |
| 5.8 | 47.60 | 1.61 | 7.77 | 21.26 |

Experiment 4

In experiment 4, the decomposition of malic acid was undertaken using the method of examples 1 and 2, but the temperature was varied to asses the effect of temperature on the levels of acrylic acid production.
Conditions:

| Precursor | 0.1M Malic Acid |
|---|---|
| Catalyst | [NaOH] - 0.05M |
| pH | 3.17 |
| Temperature | Variable |
| Residence time | 100 seconds |
| Pressure | 2500 psi |

The results of experiment 4 are shown hereunder in Table 4.

TABLE 4

| Temperature (° C.) | Malic Acid Conversion | Acrylic Acid Yield | Maleic Acid Yield | Fumaric Acid Yield |
|---|---|---|---|---|
| 280 | 57.33 | 7.87 | 18.30 | 24.77 |
| 290 | 70.40 | 13.36 | 24.48 | 32.87 |

TABLE 4-continued

| Temperature (° C.) | Malic Acid Conversion | Acrylic Acid Yield | Maleic Acid Yield | Fumaric Acid Yield |
|---|---|---|---|---|
| 300 | 81.11 | 19.09 | 26.13 | 34.98 |
| 310 | 86.76 | 27.62 | 26.44 | 34.53 |
| 320 | 90.97 | 36.97 | 23.92 | 27.12 |
| 330 | 95.90 | 41.78 | 16.11 | 12.58 |
| 340 | 95.11 | 59.23 | 10.52 | 6.88 |

Experiment 5

Experiment 5 is similar to experiment 4—decomposition of malic acid was undertaken using the method of examples 1 and 2, but the temperature was varied to asses the effect of temperature on the levels of acrylic acid production.
Conditions:

| | |
|---|---|
| Precursor | 0.1M Malic Acid |
| Catalyst | [NaOH] - 0.05M |
| pH | 3.31 |
| Temperature | Variable |
| Residence time | 100 seconds |
| Pressure | 3500 psi |

The results of experiment 5 are shown hereunder in Table 5.

TABLE 5

| Temperature (° C.) | Malic Acid Conversion | Acrylic Acid Yield | Maleic Acid Yield | Fumaric Acid Yield |
|---|---|---|---|---|
| 330 | 95.41 | 43.66 | 16.36 | 13.35 |
| 335 | 96.34 | 52.30 | 13.40 | 9.56 |
| 340 | 97.48 | 53.22 | 8.68 | 5.72 |
| 345 | 98.26 | 56.18 | 5.22 | 3.24 |
| 350 | 98.54 | 57.73 | 2.68 | 1.42 |
| 355 | 100.00 | 49.02 | 0.59 | 0.00 |
| 360 | 100.00 | 44.68 | 0.17 | 0.00 |
| 365 | 100.00 | 42.21 | 0.02 | 0.00 |

As shown in experiments 3 to 5, acrylic acid can be produced by thermal decomposition of malic acid in the presence of a base catalyst.

Advantageously, the present invention provides an alternative route to acrylic and methacrylic acid.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), onto any novel one, or any novel combination, of the steps of any method or process so disclosed.

The invention claimed is:

1. A method of producing a compound of formula (i):

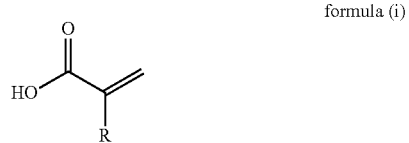

formula (i)

wherein R=H or $CH_3$
the method comprising exposing a source of a compound of formula (ii) to reaction conditions of temperature and pressure:

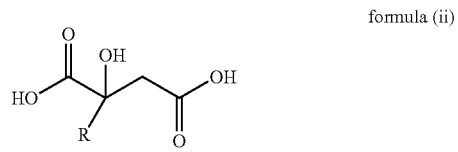

formula (ii)

wherein R is defined as above
wherein, when R=$CH_3$, the source of a compound of formula (ii) is exposed to reaction conditions of temperature and pressure while being in a liquid phase;
wherein the reaction conditions comprise a pressure in excess of atmospheric pressure and less than 10,000 psi.

2. A method as claimed in claim 1, wherein the reaction conditions comprise a temperature of at least 100° C. and less than about 450° C.

3. A method as claimed in claim 1, wherein the reaction conditions comprise a pressure of between about 200 and 10,000 psi.

4. A method as claimed in claim 1, wherein the reaction conditions comprise a temperature and pressure at which the reaction medium is in the liquid phase.

5. A method as claimed in claim 1, wherein the source of a compound of formula (ii) is exposed to reaction conditions of temperature and pressure in the presence of a catalyst.

6. A method as claimed in claim 5, wherein the catalyst is a base catalyst, an acid catalyst or an acid and base catalyst.

7. A method as claimed in claim 1, wherein the source of a compound of formula (ii) is exposed to the reaction conditions for a time period of between about 0.1 seconds and 300 seconds.

8. A method as claimed in claim 1, wherein the reaction conditions are generally acidic.

9. A method of converting citramalic acid to methacrylic acid, the method comprising exposing a source of citramalic acid in the liquid phase to reaction conditions of pressure and temperature.

10. The method as claimed in claim 1, further comprising esterification of the compound of formula (i).

11. The method as claimed in claim 1, further comprising esterification of the methacrylic acid formed by the method of claim 1 to form methyl methacrylate, followed by polymerisation of the said methyl methacrylate.

12. The method as claimed in claim 1, further comprising the steps of
(i) optional esterification of the compound prepared by the method of claim 1 to produce the corresponding ester;
(ii) polymerisation of the compound prepared by the method of claim 1 and/or the ester prepared in step (i), optionally with one or more comonomers, to produce polymers or copolymers thereof.

13. The method of claim 1, wherein the compound of formula (i) is produced from the compound of formula (ii) in one step.

14. The method of claim 1, wherein R=H.

15. The method of claim 1, wherein R=CH$_3$.

16. The method of claim 1, wherein the liquid phase is an aqueous phase.

* * * * *